(12) United States Patent
Schoonen et al.

(10) Patent No.: US 10,006,889 B2
(45) Date of Patent: Jun. 26, 2018

(54) METHOD AND DEVICE FOR RECEIVING A DROPLET

(71) Applicant: UNIVERSITEIT LEIDEN, Leiden (NL)

(72) Inventors: Jan-Willem Schoonen, Leiden (NL); Peter Lindenburg, Leiden (NL); Paul Vulto, Leiden (NL); Thomas Hankemeier, Leiden (NL)

(73) Assignee: UNIVERSITEIT LEIDEN, Leiden (NL)

( * ) Notice: Subject to any disclaimer, the term of this patent is extended or adjusted under 35 U.S.C. 154(b) by 0 days. days.

(21) Appl. No.: 14/898,833

(22) PCT Filed: Jun. 19, 2014

(86) PCT No.: PCT/NL2014/050406
§ 371 (c)(1),
(2) Date: Dec. 16, 2015

(87) PCT Pub. No.: WO2014/204312
PCT Pub. Date: Dec. 24, 2014

(65) Prior Publication Data
US 2016/0139090 A1    May 19, 2016

(30) Foreign Application Priority Data

Jun. 19, 2013 (NL) .................................... 2011009

(51) Int. Cl.
*G01N 30/12* (2006.01)
*G01N 1/28* (2006.01)
(Continued)

(52) U.S. Cl.
CPC ............... *G01N 30/12* (2013.01); *G01N 1/28* (2013.01); *G01N 1/34* (2013.01); *G01N 1/4022* (2013.01);
(Continued)

(58) Field of Classification Search
CPC ................. G01N 30/12; G01N 1/4022; G01N 2001/4027
See application file for complete search history.

(56) References Cited

U.S. PATENT DOCUMENTS 5,227,137 A * 7/1993 Monti .................... B01D 61/18
    210/406
6,461,572 B1   10/2002 Calfee et al.
(Continued)

OTHER PUBLICATIONS

Schoonen et al., Solvent Exchange Module for LC-NMR Hyphenation Using Machine Vision-Controlled Dropleet Evaporation, Anal. Chem. (2013), 85:5734-5739.
(Continued)

Primary Examiner — Paul West
(74) Attorney, Agent, or Firm — Pepper Hamilton LLP

(57) ABSTRACT

The present invention relates to a droplet receiver, comprising a receptacle for receiving a droplet, a fluid conduit connected at a first end thereof to the droplet receptacle thereby providing a course within which the droplet received in the droplet receptacle moves, the conduit at its distal end in communication with a reservoir, and a fluid layer wetting the internal walls of the receptacle and conduit in such a way as permit reception of the droplet without loss of the received droplet due to wetting of the internal receptacle and conduit walls.

20 Claims, 11 Drawing Sheets

(51) Int. Cl.
| | |
|---|---|
| G01N 1/34 | (2006.01) |
| G01N 1/40 | (2006.01) |
| G01N 30/06 | (2006.01) |
| G01N 30/64 | (2006.01) |
| G01N 30/72 | (2006.01) |
| G01N 30/46 | (2006.01) |

(52) U.S. Cl.
CPC ........... *G01N 30/06* (2013.01); *G01N 30/463* (2013.01); *G01N 30/64* (2013.01); *G01N 30/7233* (2013.01)

(56) References Cited

U.S. PATENT DOCUMENTS

| | | | |
|---|---|---|---|
| 6,620,620 | B1 | 9/2003 | Anderson et al. |
| 2003/0040114 | A1* | 2/2003 | Cui .......................... C12Q 1/25 435/455 |
| 2004/0203175 | A1* | 10/2004 | Li .............................. G01N 1/40 436/180 |
| 2010/0077874 | A1 | 4/2010 | Kanomata |
| 2012/0251999 | A1 | 10/2012 | Demirci et al. |

OTHER PUBLICATIONS

Bedani et al., Theories to support method development in comprehensive two-dimensional liquid chromatography—A review, J. Sep. Sci (2012), 35:1697-1711, (DOI 10.1002/jssc.201200070).
Bhikhabhai et al., Production of milligram quantities of affinity tagged-proteins using automated multistep chromatographic purification, Journal of Chromatography (2005), 1080(1):83-92.
Ding et al., A vacuum assisted dynamic evaporation interface for two-dimensional normal phase/reverse phase liquid chromatography, Journal of chromatography. A. (2010), 1217:5477-5483, (DOI 10.1016/j.chroma.2010.06.053).
Dugo et al., Comprehensive multidimensional liquid chromatography: Theory and applications, Journal of chromatography. A. (2008), 1184:(1-2)353-368, (DOI 10.1016/j.chroma.2007.06.074).
Erni, Two-dimensional column liquid chromatographic technique for resolution of complex mixtures, Journal of Chromatography (1978), 149:561-569, (DOI 10.1016/S0021-9673(00)81011-0).
Francois et al., Comprehensive liquid chromatography: Fundamental aspects and practical considerations—A review, Analytica Chimica Acta (2009), 641(1-2):14-31, (DOI 10.1016/j.aca.2009.03.041).
Fairchild et al., Approaches to comprehensive multidimensional liquid chromatography systems, Journal of Chromatography. A. (2009), 1216(9):1363-1371, (DOI 10.1016/j.chroma.2008.12.073).
Grob et al., On-Line Solvent Evaporator for Coupled LC Systems, HRC—Heidelberg—(1992), 15(9):594-600.
Grob et al., Concurrent solvent evaporation for on-line coupled HPLC-HRGC, Journal of High Resolution Chromatography & Chromatography Communications (1986), 9:95-101, (DOI 10.1002/jhrc.1240090208).
Grob et al., Loop-Type Interface for Concurrent Solvent Evaporation in Coupled HPLC-GC. Analysis of Raspberry Ketone in a Raspberry Sauce as an Example, Journal of High Resolution Chromatography & Chromatography Communications (1986), 9:518-523, (DOI 10.1002/jhrc.1240090906).
Grob et al., Introduction of Water and Water-Containing Solvent Mixtures in Capillary Gas Chromatography: IV. Principles of Concurrent Solvent Evaporation with Co-Solvent Trapping, Journal of Chromatography (1989), 473:411-422, (DOI 10.1016/S0021-9673(00)91325-6).
Hyotylainen, Critical evaluation of sample pretreatment techniques, Analytical and Bioanalytical Chemistry (2009), 394(3):743-758, (DOI 10.1007/s00216-009-2772-2).
Jandera, Comprehensive Two-Dimensional Liquid Chromatography—practical impacts of theoretical considerations. A review., Central European Journal of Chemistry (2012), 10(3):844-875, (DOI 10.2478/s11532-012-0036-z).
Jonsson, On-chip membrane extraction in analytical sample preparation: II. Applications, Trac-Trends in Analytical Chemistry (1999), 18:325-334 (DOI 10.1016/S0165-9936(99)00103-X).
Jonsson, On-chip membrane extraction in analytical sample preparation: I. Principles, Trac-Trends in Analytical Chemistry (1999), 18:318-325, (DOI 10.1016/S0165-9936(99)00102-8).
Lindenburg et al., On-line large-volume electroextraction coupled to LC-MS to improve detection of peptides, Journal of a Chromatography A Manuscript Draft (2012), 1249:17-24, (DOI 10.1016/j.chroma.2012.06.016).
Lindenburg, Feasibility of electroextraction as versatile sample preconcentration for fast and sensitive analysis of urine metabolites, demonstrated on acylcarnitines, Electrophoresis (2012), 33:2987-2995, (DOI 10.1002 elps.201200276).
Moret et al., On-Line Solvent Evaporator for Coupled LC Systems: Further Development, J. High Resol.Chromatogr. (1996), 19(8):434-438.
Petersen' On-chip electromembrane extraction for monitoring drug metabolism in real time by electrospray ionization mass spectrometry, Analyst (2012), 137:3321-3327, (DOI 10.1039/C2an35264h).
Petersen, On-Chip Electro Membrane Extraction with Online Ultraviolet and Mass Spectrometric Detection, Anal Chem (2011), 83:44-51, (DOI 10.1021/Ac1027148).
Petersen et al., Drop-to-drop microextraction across a supported liquid membrane by an electrical field under stagnant conditions, Journal of Chromatography A (2009), 1216:1496-1502.
Stichlmair et al., Electroextraction: A Novel Separation Technique, Chemical Engineering Science (1992), 47(12):3015-3022, (DOI 10.1016/0009-2509(92)87003-9).
Tian et al., Multidimensional liquid chromatography system with an innovative solvent evaporation interface, Journal of Chromatography A (2006), 1137(1):42-48, (DOI 10.1016/j.chroma.2006.10.005).
Tian et al., Vacuum-evaporation Interface of Comprehensive Two-dimensional Liquid Chromatography and Its Application, Chin J Anal Chem (2008), 36(6):860-864, (DOI 10.1016/S1872-2040(08)60044-4).
Tian et al., Comprehensive two-dimensional liquid chromatography (NPLC X RPLC) with vacuum-evaporation interface, J. Sep. Sci. (2008), 31(10):1677-1685, (DOI 10.1002/jssc.200700559).
Vulto et al., Phaseguides: a paradigm shift in microlluidic priming and emptying, Lab on a Chip (2011), 11(9):1596-1602, (DOI 10.1039/C0lc00643b).
International Search Report and Written Opinion for PCT/NL2014/050406 dated Apr. 9, 2015.

\* cited by examiner

METHOD AND DEVICE FOR RECEIVING A DROPLET

CLAIM OF PRIORITY

This application is a U.S. national stage filing under 35 U.S.C. § 371 of International Application No. PCT/NL2014/050406 filed on Jun. 19, 2014 entitled "METHOD AND DEVICE FOR RECEIVING A DROPLET," which claims priority from Netherlands Patent Application Number 2011009 filed on Jun. 19, 2013, both of which are incorporated herein by reference in their entirety.

FIELD OF THE INVENTION

The subject invention relates to a method and a device for the processing of analytical samples and selective solvent removal from liquid analytical samples in (bio)chemical analysis.

The subject invention may advantageously be used to improve the resolution of multi-dimensional chromatographic separations, to avoid or reduce solvent interference in NMR and electrospray-MS and to improve biochemical assays like, among others, enzyme assays.

The subject invention lends itself particularly well for low sample flow rates and small sample volumes.

Furthermore, the invention can be used to remove solvents from a sample or sample stream where solvents may interfere in a subsequent step. Such interferences include the presence of protonated eluents in NMR detection or the presence of non-aqueous solvents which have negative influences in bio-assays, such as protein denaturation.

The method is particularly suitable for very small liquid flow rates commonly less than 5 mL/minute.

Structural identification of compounds in complex mixtures is a recurrent problem in chemistry and the life sciences. In chemistry, molecular characterization is a requirement for understanding compound reactivity and stability. Furthermore, in the life sciences structural elucidation of biomolecules in formulations and biofluids is a prerequisite for understanding biological mechanisms of action.

In the emerging field of metabolomics, the identification of metabolites has become a critical step. One major bottleneck in molecular identification in complex mixtures is to obtain sufficient molecular separation and enrichment to enable structural elucidation or confirmation by spectrometric and spectroscopic techniques. For unambiguous structural elucidation it is crucial to combine the complementary information provided by e.g. NMR and mass spectrometry (MS), especially if reference compounds are not available. Whereas effective LC-MS and GC-MS interfaces have been designed in the last decades, the hyphenation of LC with NMR remains cumbersome. The largest technical drawbacks are the inherent insensitivity of and the large background signals produced by common LC eluents. There is a long history of attempts to overcome these hurdles. On-flow LC-NMR applications were already described three decades ago but found only limited use due to low sensitivity, high deuterated solvent consumption, and inefficient solvent signal suppression techniques. The use of LC-NMR in the stopped-flow mode is more widespread, but this method typically compromises molecular separation. US2010/0196209 A1 discloses a method for dispensing in a reaction vessel and reaction vessel processing apparatus. Herein, a droplet of a low volatile liquid, specifically a mineral oil is dispensed onto a reaction solution previously dispensed to a probe arrangement part; a liquid droplet of the mineral oil is then formed on the tip end of a nozzle, and the liquid droplet is transferred into a reaction well while it is in contact with the inner wall face of the reaction well or the surface of the reaction solution previously dispensed to the reaction well. Moving of the droplet may be an issue involving loss of the droplet; furthermore, the transferred droplet cannot be introduced into a secondary separation process, and due to solvent composition changes, the resolution offered by quantitative LCxLC is likely impossible to attain.

US-A-2004/203175 discloses an apparatus and a method for concentrating and collecting analytes from a flowing liquid stream. This is performed by an apparatus for concentrating and collecting one or more analytes in a flowing liquid stream of a carrier solvent composed of one or more solvent components. The apparatus includes a transfer tube which forms one or more aligned bores, each having an inlet and an outlet, the inlet being adapted to accept the flowing liquid stream, and the outlet being adapted to form continuously replaced, hanging droplets of the liquid stream. The apparatus also includes a collection device mounted below the outlet of the transfer tube for collecting the droplets. The apparatus includes a device for heating the liquid stream in the transfer tube to a temperature sufficient to cause partial evaporation of the carrier solvent from the hanging droplets but not exceeding the boiling point of the carrier solvent; and a device for heating the collection device to a temperature sufficient to cause further evaporation of the carrier solvent. In the above-described method, the samples may be evaporated to dryness leading to potentially severe analyte loss and/or analyte degradation. A further issue resides in the fact that since the evaporated sample volume may change during gradient runs, due to solvent composition changes, the resolution offered by quantitative LCxLC may be jeopardized.

Accordingly, here remains a need for improving the chromatographic separation power of LCxLC systems, without the issues raised above.

Similarly presently there is no automated system that permits coupling of an LC unit is coupled to other analytical means, such as for instance NMR, or mass spectrometry, the presence of the elution solvents may cause issues, or disturb the measurement, such as ion-suppression in mass-spectrometry.

Hence, there is a significant need for a technology that facilitates the exchange of eluent types while the aforementioned negative effects are significantly decreased or eliminated. More specifically, there remains a need for a technique that allows rapid and effective handling of small samples and easy solvent exchange without significant loss of solutes due to surface wetting, and without rediluting the sample largely. Accordingly, in a first aspect, the present invention relates to a droplet receiver, comprising a receptacle for receiving a droplet, a fluid conduit connected at a first end thereof to the droplet receptacle thereby providing a course within which the droplet received in the droplet receptacle moves, the conduit at its distal end in communication with a reservoir, and a fluid layer wetting the internal walls of the receptacle and conduit in such a way as permit reception of the droplet without loss of the received droplet due to wetting of the internal receptacle and conduit walls, wherein the droplet receiver further comprises means for applying reduced pressure to draw the received droplet into the reservoir.

In a further aspect, the subject invention relates to a device for selective solvent evaporation from a liquid feed, the feed comprising one or more components diluted in at least a first solvent or a solvent blend, comprising a) A first tubular vessel having a distal end or a channel suitable for the formation of a droplet of a first volume, at an inflow rate $r_1$, at the tip or in the lumen of the tubular vessel, and b) means for subjecting the droplet to a solvent evaporation step at an evaporation rate $r_2$ to evaporate at least part of the first solvent or solvent blend, and to accumulate the components in the feed in the droplet during the evaporation process at an accumulation rate $r_3$, to obtain a concentrated feed volume in the droplet, and c) A droplet receiver according to the invention.

In a further aspect, the subject invention relates to an arrangement for the multi-dimensional separation of a liquid feed comprising one or more components, comprising:

i) at least a first separation device for the separation of compounds in the sample diluted in a first solvent or solvent blend in a first dimension into a first liquid feed comprising one or more components; and ii) A device for selective solvent evaporation from the first liquid feed to obtain one or more concentrated droplets, and iii) A droplet receiver, and iv) at least a second separation device for the separation of the components in the received concentrated sample droplets in a second dimension, and/or v) a device for analysing the components in the concentrated droplets.

In yet a further aspect, the present invention relates to a process for the selective solvent removal from a liquid feed comprising one or more components diluted in at least a first solvent or a solvent blend, comprising the steps of:

a) forming an amount of the feed derived from a first separation device into a droplet with a first defined volume at the distal end or within a tubular vessel at a defined inflow rate $r_1$ at the tip of the capillary or in the channel, and b) subjecting the droplet to a solvent removal step to remove at least part of the solvent or solvent blend at a defined solvent removal rate $r_2$ to remove at least part of the first solvent or solvent blend, and accumulation of components in the sample in the droplet during the solvent removal process at a rate of the accumulation $r_3$, to obtain a concentrated feed droplet.

BRIEF DESCRIPTION OF THE FIGURES

Hereinafter, droplet receivers and methods of receiving droplets according to the preferred embodiments of the present invention will be described in detail with reference to the accompanying drawings. Reference now should be made to the drawings, in which the same reference numerals are used throughout the different drawings to designate the same or similar components, and the duplicate description of the components will be omitted. Herein, terms such as an upper portion or a lower portion are used to distinguish components from each other, and the components are not limited to the above terms. These and further features can be gathered from the claims, description and drawings and the individual features, both alone and in the form of subcombinations, can be realized in an embodiment of the invention and in other fields and can represent advantageous, independently protectable constructions for which protection is hereby claimed. Embodiments of the invention are described in greater detail hereinafter relative to the drawings, wherein:

DETAILED DESCRIPTION OF THE INVENTION

Figure 1:
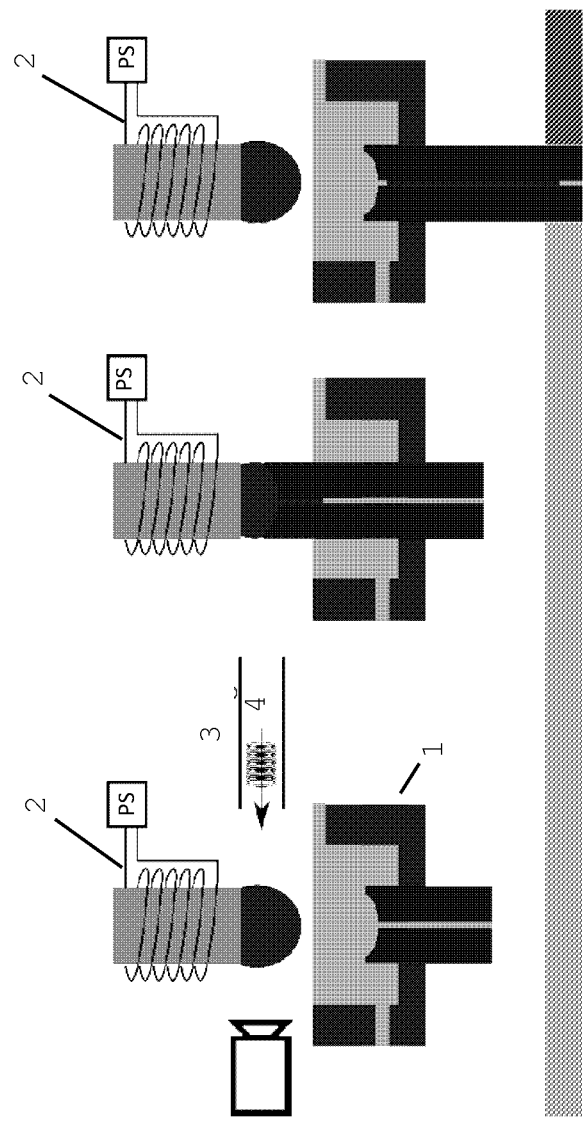
FIG. 1 is a sectional view illustrating a droplet receiver (1) according to the preferred embodiment of the present invention, when receiving a droplet, also showing a pre-heater (2), and a means for providing a flow of heated gas (3), such as $N_2$ (g) (4).
Figure 2:
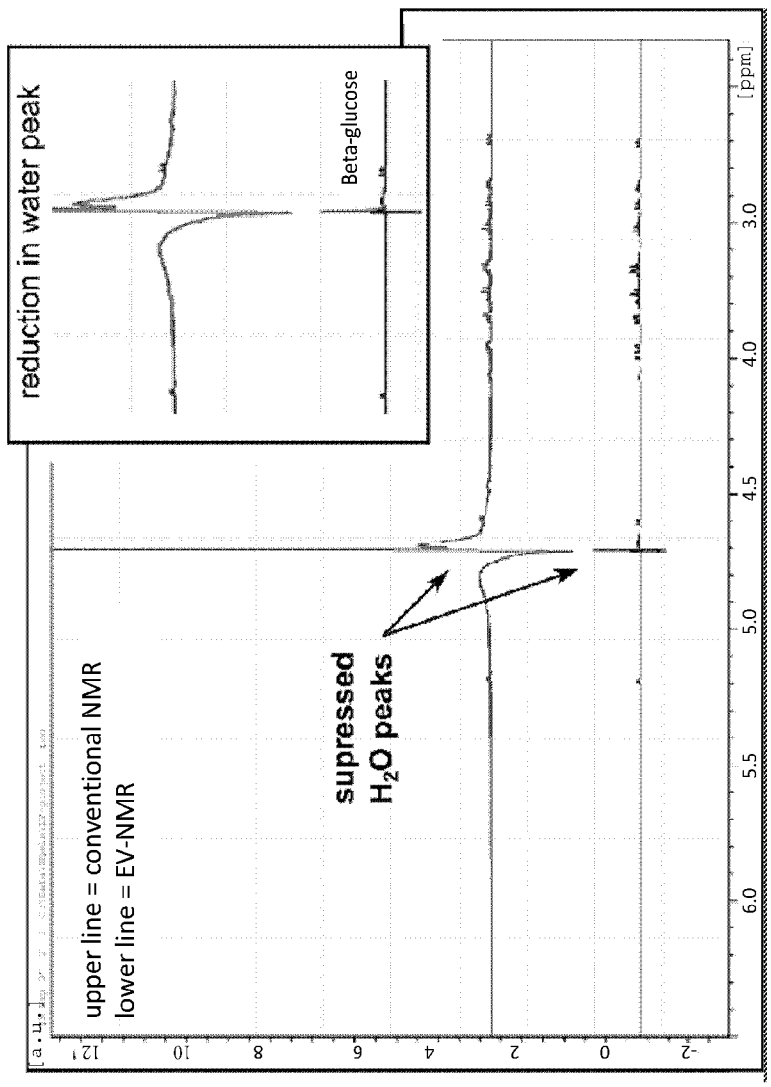
FIG. 2 shows a comparison of NMR spectra obtained from a conventional solvent switch process and from the subject process; x-axis plotting frequency, in ppm, and y-axis intensity, in a.u., showing a reduction in a water resonance peak for Beta Glucose.
Figure 3:
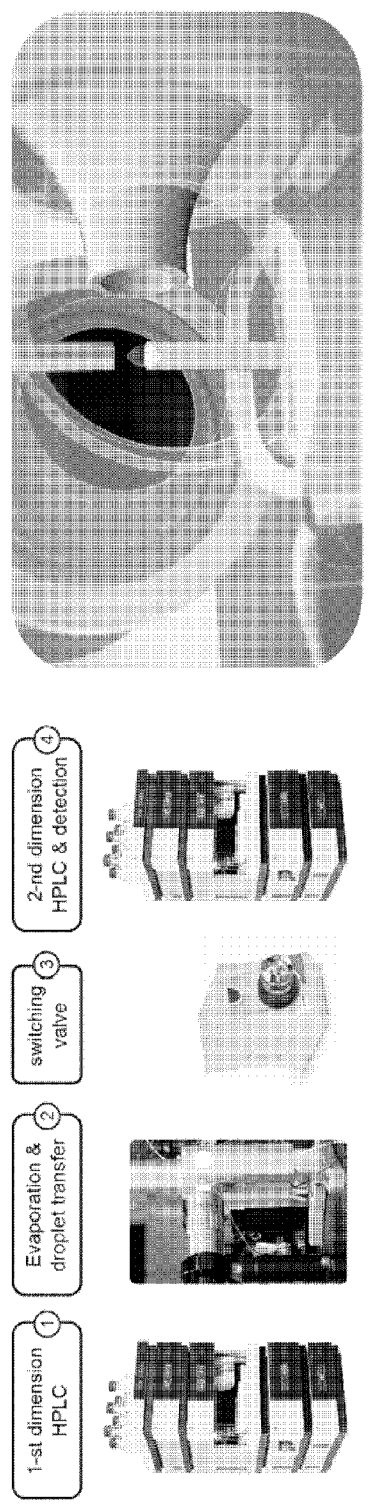
FIG. 3 shows a depiction of a preferred embodiment of a system operating the receiver according to the invention in an LCxLC operation.
Figure 4:
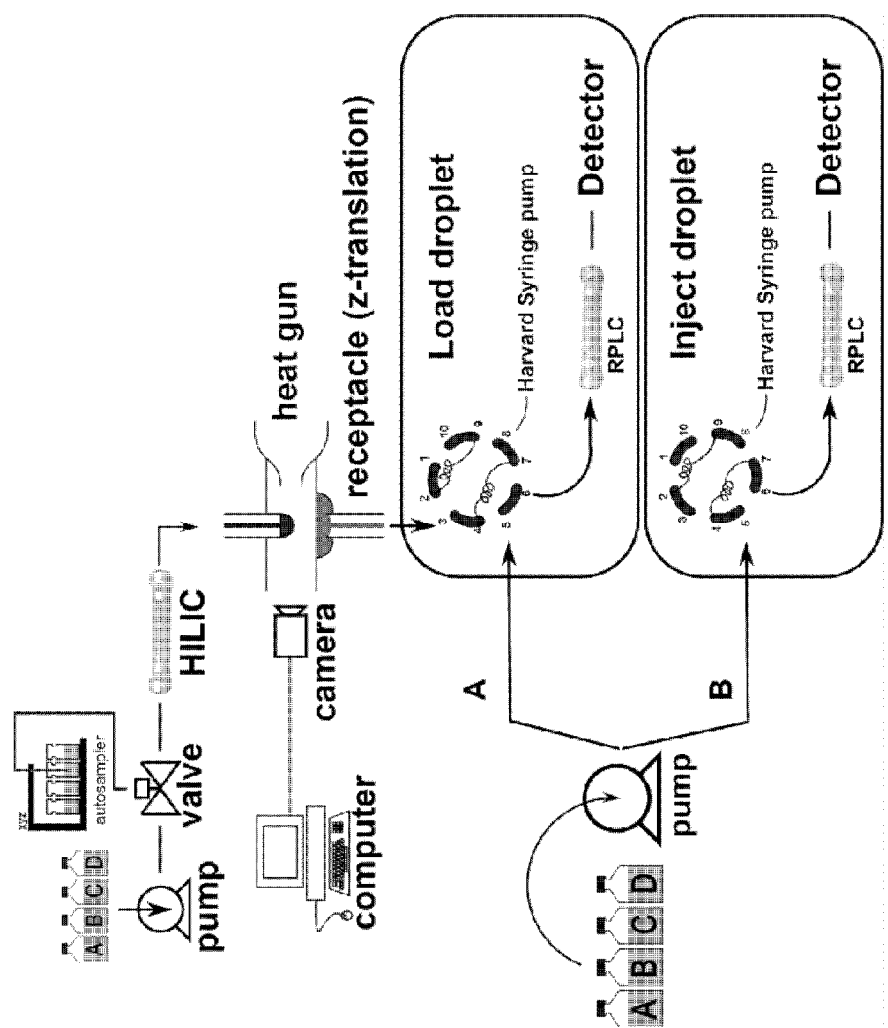
FIG. 4 shows a schematical representation of the machine vision controlled effluent evaporation system.

The present invention relates to a droplet receiver, process, device and arrangement, all directed at a selective solvent switch process from sample droplets obtained from a liquid feed.

The present invention allows to selectively transfer droplets comprising analytes, such as samples derived from complex mixtures of analytes, for instance chemical or biochemical components, in particular those that have been subjected to a separation into compounds in a first separation treatment.

The sample itself may comprise a single component, or a mixture of components which may be complex.

The reservoir of the droplet receiver further comprises means for applying reduced pressure to draw the received droplet into the reservoir. This may be advantageously done through the use of a switch valve that permits to apply vacuum or reduced pressure to the receptacle, thereby drawing the received droplet into the reservoir.

Preferably, the droplet receiver is mounted on a support movable at least in an up- and downward direction, and wherein the uppermost position permits to contact a pendant droplet. The internal space of the receptacle is preferably shaped such that a sectional area thereof is reduced towards the conduit.

The fluid layer is preferably a liquid layer exhibiting a flow; hence the Droplet receiver preferably further comprises a fluid feeding unit.

The fluid feeding unit may preferably comprise a fluid bath for submerging the recipient when not receiving a droplet; the bath preferably being provided with an inlet and an outlet for the circulation of the fluid.

The reservoir preferably comprises a valve at the reservoir and a second conduit in fluid communication with the valve, to direct a plug flow of a received droplet to a further analysis or separation process; the reservoir optionally comprising a fluid overflow conduit for reverting fluid back to the fluid feed.

The solvent removal is preferably performed by evaporating the solvent(s). This evaporation process can be mathematically modelled as a flow process where the flows can be mass flows (kg/s), mole flows (mole/s), volume flows (L/s) or other flows suitable to describe the process.

In the present process, $r_1$ is the rate of inflow of a sample, $r_2$ is the rate of solvent removal, preferably through evaporation, and $r_3$ is the rate of the accumulation of compounds in the liquid volume remaining in the droplet during the evaporation process. Due to the conservation of mass, the flow of compounds through the device is set out in general formula I:

$$r_1 = r_2 + r_3 \quad (I)$$

In the case that there is more than one compound present in the liquid, e.g. a dissolved species B in a solvent A, different flow balances can be formulated as in formula IIa and b:

$$r_{1,A} = r_{2,A} + r_{3,A} \quad (IIa)$$

$$r_{1,B} = r_{2,B} + r_{3,B} \quad (IIb)$$

If more compounds are present, a flow balance equation is added for each compound species.

The term "liquid feed" herein refers to a fluid under conditions of the process/separation method. The feed arrives at the tubular vessel in liquid phase, wherein preferably all components are dissolved. This may be a normally liquid solvent or solvent blend, or it may one or more supercritical gases, e.g. liquid carbon dioxide.

The term "feed" refers to a volume or aliquot of fluid as set out above passing through the separation process prior to entry of device/process according to invention.

The liquid feed typically is a liquid aliquot of a feed comprising one or more components, typically of a complex analyte mixture. The components may be complex compounds, mixtures or salts thereof, however may also be pure chemical compounds. Typically the subject process would be ideally employed to separate a complex analyte mixture into its constituent components. The term "comprising" has the meaning of also entailing the term "consisting" within the present specification.

A droplet as described herein above refers to a meniscus, droplet sheet or a hemisphere droplet. The droplet is a small element of liquid, bounded almost completely by free gas/liquid surfaces with the exception of the surface boundary provided by the distal end of the tubular vessel.

The droplet is formed when liquid accumulates in the vessel in the case of a meniscus, or a pendant or standing droplet in the case of a tip of a tubular vessel or a droplet sheet in the case of for instance an elongated channel at the end of the vessel, as for instance provided by a channel etched into a microfluidic chip. If the vessel, the distal end of the vessel or the channel are pointing essentially downward, this will likely result in a pendant droplet, meniscus or droplet sheet, all of which will be referred to as "droplet" herein.

A pendant droplet is suspended from the end of a tube by surface tension. Alternatively, the droplet may be formed by pushing a liquid upward through an essentially upward pointing distal end of the capillary vessel, or vessel itself thereby forming a standing droplet. Preferably the droplet is a Pendant droplet, since this minimizes surface to volume ratio and prevents drying out.

Under the term "liquid feed" herein is to be understood any feed comprising a solvent or blend which is a fluid at the conditions of the process. The sample may be a liquid feed comprising dissolved components or components that are suspended or emulsified in a liquid medium.

The device according to the invention employs a first tubular vessel having as an outlet a distal end or a channel suitable for the formation of a droplet of a first volume.

The term "feed" refers to a volume or aliquot of fluid as set out above passing through the separation process prior to entry of device/process according to invention.

The term "tubular" vessel herein refers to an essentially tubular structure that comprises an outer surface, an inner surface and a lumen at the inside of the structure. The cross-sectional shape of the tubular wall structure may be circular, or square, or of a non-specifically defined geometry. The specific geometry of the cross-section is not considered as relevant, provided that the tubular device is suitable for transferring fluids, such as for instance also applicable for channels etched in a microfluidic chip.

The tubular vessel has a defined lumen through which the solvent and sample are pumped.

Preferably, the tubular vessel is a capillary tube having an inner diameter of less than 5 mm, measured as the diameter between the largest distances.

Suitable wall materials are essentially inert with respect to the solvents and/or the components carried in the liquid feed, and are further not deformed at the temperatures or conditions employed in the subject device. Typical materials include silicon, metals and/or alloys such as gold, copper or stainless steel, glasses and thermoset polymeric materials such as cross-linked epoxy resins, poly methyl methacrylate, Cyclo-olefin (co)polymers, polyimide, fluoro-ethylene polymer and/or polycarbonate.

The device according to the invention preferably further comprises means to adjust at least two of $r_1$, $r_2$ and/or $r_3$. Preferably, the device comprises means to adjust pressure, temperature and/or gas flow rate at the gas/liquid interface of the droplet. Additionally the vessel leading to the distal end may be heated to pre-heat the solvent going into the droplet and aid a more rapid evaporation process.

Preferably, in the device according to the invention, $r_1$, $r_2$ and/or $r_3$ are controlled by an automated system. Preferably, the automated system comprises at least one or more sensors, and/or one or more actuators.

The device according to the invention further preferably comprises a comparison means that correlates sensor data to a set point value, and delivers an adjustment signal to an actuator to adjust the magnitude of the parameter controlled by the actuator, wherein the actuator controls evaporation rate $r_2$.

The term "actuator" herein refers to any suitable means to control any of the controllable parameters of the system, e.g. temperature, pressure, flow rate of the liquid feed, which result in controlling of solvent evaporation rate $r_2$.

The term "sensor" herein refers to any suitable means for measuring a parameter of the system, e.g. temperature, pressure, flow rate of the liquid feed.

Preferably, the automated control system comprises a machine vision unit that sequentially acquires one or more images of the droplet, processes the acquired images to determine one or more droplet parameters; and communicates the parameters to a comparison means. One or more droplet parameters include the surface integral and/or the diameter of a droplet, which at a given droplet shape can be linked to the droplet volume.

Preferably, the machine vision controlled evaporation system comprises of a camera which continuously monitors the droplet width. From the droplet width, the droplet volume can be calculated by using a droplet width to droplet volume calibration graph. This calibration graph can easily be obtained by plotting the true droplet volume deduced from a known liquid feed against the measured droplet width. A light source is used to create a droplet silhouette which facilitates edge detection of the droplet. The continuous size of the droplet is monitored by a proportional integral derivative which calculates the amount of heat which is needed to maintain a steady state droplet volume/shape.

In this setup, the use of a camera together with the PID control loops permits the evaporation interface operate independent of solvent flow and solvent composition within physicochemical limits. This makes the interface suitable for a wide variety of columns and elution programs without the need of complicated knowledge on solvent properties and other evaporation parameters. Furthermore, the camera can be used for means of process control, e.g. droplet fall off, droplet discolouring, droplet shape shifting etc). Periodically, the droplet must be transferred towards the second separation dimension. This has been realized by using a receptacle which consists of a stainless steel tubing (ID 0.125 mm×cm long) which is connected to a switching valve with a 10 µL loop installed on it. A syringe pump is used to draw the hanging droplet and transfer it in the loop which is subsequently switched. The receptacle is placed in a continuously refreshed solvent bath in order to flush the receptacle and its connected tubing prior every injection to ensure contamination free injections. The total volume of the tubing is kept at a minimum and the draw speed is maximized in order to minimize sampling times while the computer controls allow easy method integration and full control (speed, sampling frequency, intra injection flushing etc.

The setup may be used for enriching samples originating from a solvent flow being either HPLC effluent or a flow injection analysis (FIA) feed. A solvent switch, if needed, can be realized by re-substituting the droplet in any other solvent system as long as the maximum concentration is not exceeded when the formation of salts will be problematic. Droplet injection volumes of 100-1000 nL could easily be introduced, and were found to be acceptable volumes for column ID's around 0.5 mm and above.

The device and arrangement according to the present invention preferably operate in an automated or closed loop manner.

The liquid feed composition may be controlled via a further sensing means, e.g. preferably a sensor detecting the presence of certain components in the feed. The gas out flow may be controlled and measured as well by sensing means, e.g. measuring the thermal conductivity of the gas. The system may further comprise different sensors at any suitable position in the device to allow additional measurements.

This ideally also contains a computing unit that is equipped with the necessary means for acquiring and interpreting the pictures taken, for calculating the droplet volume, and for controlling both the solvent eluent speed as well as the evaporation rate through control of the gas flow and/or heater unit. In this way, droplet size and evaporation rate may be linked to each other, and controlled and monitored to match the eluent feed rate of the primary column The monitoring preferably is performed by the droplet or meniscus being monitored by a camera set-up. Preferably the camera setup is coupled with a computer running a machine-vision programme capable of monitoring droplet size, droplet colour, droplet growth, and/or meniscus position.

Preferably the computer is also coupled in a feedback mode to the heater, thus controlling droplet growth and/or meniscus position. More preferably, the machine vision programming is capable of monitoring artefact occurrence such as precipitation, discolouring, droplet fall-off, droplet distortion, air bubble formation in the droplet, crystal formation, boiling or other effects that occur during the evaporation. Preferably, visual information of droplet formation, the evaporation process and the transference process that is monitored by a camera set-up is stored on the computer for validation check up of the experiment. Yet more preferably the method for image analysis comprises pixel count, line integral, edge detection and/or curve fitting.

Alternatively, the droplet or meniscus is monitored by other measurement techniques, such as capacitive, conductive, refractive index, or mass monitoring. This preferred embodiment may be used in a constant droplet-size mode, preventing for instance dry-cooking of the sample. In this constant droplet size mode, a droplet will be maintained at a certain defined volume, whereby the evaporation will increase the amount of solute in the droplet.

The subject device and arrangement may be employed to simply control the formation of liquid volumes, e.g. if only samples that likely contain desired compounds are being evaluated, while others not containing the compounds are removed immediately. This is the case if $r_2$ is close or equal to 0, such that $r_1$ becomes equal to $r_3$. An example of such a process is one where several compounds have been separated by an LC process.

Subsequently, only those droplets containing the desired compounds may advantageously be subjected to solvent evaporation, while the remainder of the droplets may be discarded. The presence of the desired components may advantageously be determined by a sensor or detector, either prior to the subject device, or in the subject device.

The feed comprises the components in a diluted form, i.e. in a dissolved or suspended state in a first solvent or a solvent blend. The first solvent or solvent blend comprises solvents that are useful as moving phase or eluents in the first separation process.

Suitable eluting solvents, also referred to as eluents, for use in the present invention include, but are not limited to water, such as deionized water, and primary alcohols, such as methanol and ethanol; aqueous or alcoholic solvent mixtures, such as, for example, hexane/isopropanol/acetonitrile. Eluent combinations suitable for certain columns and separations are well known in the art. Additional suitable eluents can be used and techniques to determine such eluents are known to those of skill in the art. An explanation of eluents and moving and stationary phase is given in the "Adsorptive Separation" section of the Kirk-Othmer Encyclopedia of Chemical Technology.

The present invention specifically represent an improvement in the integration of Multi-dimensional liquid chromatography (MDLC), which is a powerful technique for unravelling complex samples. Although introduced already three decades ago, the theoretical separation capacity of MDLC systems is however hardly achieved in practice.

Unlocking the true separation power of MDLC systems would not only be highly beneficial for the analysis of very complex samples, it would also significantly reduce ion-suppression and increase the quality of Mass Spectrometry (MS) data if coupled to a MS apparatus. Furthermore, the ease and speed of method development in comparison to uni-dimensional approaches for group separations would be an advantage. Hence, there are many advantages and reasons making MDLC an interesting technique and justifying the technical development of new MDLC systems, as the separation power of MDLC systems would be highly beneficial for analytical point of view because the peak capacity is a product of the separate column peak capacities rather than the sum.

This leads to spectacular separation capacities, especially when multiple dimensions can be coupled, within maximum but realistic laboratory analysis lead times.

Applicants found however that MDLC peak capacity theory is often not achieved in practice due to solvent incompatibilities, dilution, peakband broadening effects and time constraints.

For instance, a weak eluting solvent from the first dimension column may be a strong eluting solvent on the second dimension column causing analytes to elute fast and with nearly identical k-factors.

HPLC is a dilutive technique with peak band broadening effects along the migration path which are worsened in MDLC due to the added loops and switching valves.

Since the secondary separation column often has a larger internal diameter in comparison to the first separation column, dilution hampers the detection even to a greater extend. Basically the chromatographer has to choose the trade-offs between maximal injection volume, optimized chromatography, detectability and time constraints. Many papers have been published on finding the optimal system settings (e.g. compatible solvent systems, peak identification procedures, modulation time calculations and maximized peak capacities. A major concern however is that ever since the introduction of MDLC, only a few papers have appeared regarding technical improvements of MDLC systems in general but especially on the modulation techniques. Although commercially available, off-line MDLC systems have the capacity of separating very complex samples already. There is a strong need for technically improved on-line comprehensive MDLC systems. Typical run-times of off-line MDLC systems can consume up to days which means these methods are of little use when many thousands of samples need to be analyzed (which is even more problematic when these samples are unstable). The majority of MDLC systems consist of parts that have been designed for the purpose of uni-dimensional separations. Obviously, the modulation technique plays a crucial role in any multi-dimensional separation system. In our vision, efforts should be aimed at improving the modulation/interfacing part of the MDLC systems the most. In this paper we present an automated and easy-to-use interface (both isocratic or gradient systems) which is dedicated to: introducing µL-sized fraction volumes; with minimal eluent incompatibilities; enriched analyte concentrations; the handling of polar and nonpolar analytes in one run; and an extension of the second separation dimension time window.

Currently, the peak separation capacity of comprehensive GCxGC is superior to that of comprehensive LCxLC. The cryogenic modulation technique is successful because it selectively refocuses analytes (and not mobile phase) from fractions and rapidly injecting them as a sharp analyte zone into the second separation dimension via computer controls. The computer controls are versatile and accurate, the analytes descending from the fraction are increased in concentration and the second separation dimension is more or less decoupled in time from the first separation dimension. Together the GCxGC modulation is subtle and potent in contrast to the GCxGC modulation technique. The LCxLC modulator is mostly a switching valve being equipped with loops, guard column loops or even columns on which the fractions are injected prior further separation/detection. Unlike the GCxGC modulator, the LCxLC modulator does not selectively refocus analytes into a small bandwidth. The analytes keep retained in the original eluting solvent which poses a deterioration of the second dimension chromatography. To minimize perturbed chromatography due to solvent mismatches, one can inject only a small part of the fraction. The chromatography is improved but the detection becomes an issue. By using a loop packed with stationary phase it is possible to focus analytes into a small zone but then analyte polarity will cause problems. Last but not least, the sample loop size plays an important role on the modulation frequency which is inversely coupled to the chromatographic performance. A small injection loop is filled faster than a large injection loop which means there is less time to fulfil a separation on the second separation dimension. However a large loop also means the maximum injection volume is most probably exceeded leading to broad peaks and subsequently deteriorates the peak separation capacity. An approach to resolve this issue comprised concurrent evaporation as a technique to evaporate large effluent volumes and retain analytes in a packed bed capillary was developed to exchange LC solvent and modulate LCxLCxGC, as disclosed for instance in K. Grob, B. Tonz, Hrc-J High Res Chrom, 1992, 15, 594-600. H. Z. Tian, J. Xu, Y. F. Guan, J Sep Sci, 2008, 31, 1677-1685, applied a specific closed loop interface to the same purpose.

While both techniques show that evaporation is useful for enriching analytes while exchanging the solvent and thereby bridging the gap in MDLC modulation, they are not sufficient to meet efficient LCxLC modulation demands, whereby an efficient LCxLC modulator should retain/concentrate analytes of both polarities in a small space, diminish solvent incompatibilities (e.g. eluting power, viscosity), be able to inject the retained analytes within a small time frame, pressure resistance (e.g. 1000 bar), handle multiple types of columns, solvents and methods, increase the second dimension separation window and be able to exploit versatile computer controls.

And of course, the modulator must operate reproducible and accurate and not introduce contaminations. A further approach includes cryogenic GCxGC modulator. Note however that this technique appears not be an option for modulation of LC columns because of the difference in properties between gasses and liquids involved.

Accordingly, applicants have now developed a solvent exchange system according to the invention which can evaporate a wide variety of LC solvents, within physico-chemical limits but regardless of solvent composition and flow rates.

For instance by ambient evaporation of a droplet the injection volume and peakband broadening are kept to a minimum, while a concentrative effect takes place and both polar and non-polar compounds can be retained the droplet can be monitored by a camera which can control the evaporation process independent of solvent composition and flow rate. Accordingly, the droplet receptacle according to the invention was allowed to realize a fast capture of a droplet, and transfer it into the next separation dimension.

Generally, in the case of coupled chromatographic processes, such as LCxLC, the first and second solvent mixtures are intended to provide orthogonal separation behaviours. For instance where a highly polar solvent or solvent blend is employed as eluent in the first separation, the second column will require an apolar solvent or solvent blend. In existing LCxLC systems, the presence of remaining solvent in the sample causes an issue with the polarity of the second separation, thereby reducing the resolution of the secondary separation. Accordingly, the first and second solvent or solvent blends at least differ in polarity.

Preferably the solvents may also be useful for a different analytical or separation method, for instance if an NMR system is coupled to the subject apparatus, the second solvent blend may be a deuterated solvent, allowing to reduce the amount of deuterated solvent required in the system, or in the case of e.g. a bioassay, solvents are evaporated that are harmful for the effectiveness of the method.

Flow rates $r_1$ and $r_2$ may advantageously be determined as follows:

The in-flow into the tubular vessel can be determined, for instance through the use of a calibrated pump or other means that measure and control the actual flow. If a second mass flow, either $r_2$ and/or $r_3$, is determined, the missing mass flow rate, respectively, can be calculated to allow control of the complete evaporation process.

The determination of $r_2$ and/or $r_3$ may be done by a variety of sensors, comprising gravimetric determination, optical detection methods, methods using electromagnetic radiation, conductimetric determination, and others.

If preferably the evaporation is done by a heated gas flow, a gas flow sensor, for instance a mass flow sensor may be positioned in the effluent gas stream leading the evaporated solvent away from the heating area, which after calibration can be used to determine the exact amount of solvent removed.

Another preferred method may use a method to determine the size of the droplet, by for instance the deflection of a laser beam passing through a hanging droplet. Still another preferred method comprises use of a camera to obtain pictures of a hanging droplet or meniscus. By determining the size and position of said droplet, droplet sheet or meniscus, the volume of the remaining liquid may advantageously be determined. When two determinations are done in succession over a known time period, this permits to determine the mass flow rate into the remaining liquid volume.

In a particularly suitable method, the camera element is attached to a computer system which analyzes the images taken, and uses an algorithm to calculate the size and position of the droplet, meniscus and/or sheet, e.g. by integration of the pixel count corresponding to a surface area.

An advantage of such a method is that the camera system does not need to be calibrated for volume measurements.

This determination of the other flows may preferably be done with a sensing system which determines the outflow of evaporated gases. Another preferred option comprises a sensing system which determines the volume of liquid present in the evaporation zone, specifically in the case of a pendant hanging droplet or a droplet sheet, or which determines the position of a liquid meniscus.

Generally, many different sensing systems may suitably be used to determine the size of a hanging droplet or droplet sheet. These sensing systems may detect directly, for instance by non-contacting means as in an optical system.

The sensing systems may advantageously be based on electromagnetic principles, optical principles, mass principles, acoustic principles, mechanical principles, thermal principles and/or other principles known to people skilled in the art.

However in case such sensing systems are dependent on the bulk solution properties of the liquid in the droplet, e.g. refractive index, optical absorbance or transmission, electrical or thermal conductivity such sensing systems will not only measure a signal resulting from the size of the droplet, but also of the changes in the bulk properties of the droplet during the whole process. As such these sensing systems will determine 'real' signal components corresponding to the droplet size, but also a 'parasitic' signal component corresponding to the droplet bulk properties. The parasitic signal component may result in erroneous behaviour of the control system which steers the evaporation process. Examples for occurrences that may result in a parasitic signal include refractive index changes, the crystallisation of compounds in a droplet, and phase changes of emulsions or dispersions.

Preferably, therefore, the system according to the invention therefore uses sensing systems which are relatively insensitive to the abovementioned solvent bulk properties, such as a system comprising a camera system with image recognition and image processing, i.e. machine vision capabilities.

The machine vision system may be employed to generate a control system for the evaporator module in which the droplet is present.

The camera system preferably may then detect the size of the droplet and sends a signal to increase the evaporation rate in case the droplet grows in size and sends a signal to decrease the evaporation rate in case the droplet decreases in size. In case the droplet volume is the same as the 'set value' the control signal is held constant. If the machine vision system is fast, i.e. performing many image acquisition and processing cycles per time period and if the evaporator module is fast the evaporation of the droplet can be controlled adequately.

Preferred options for image processing include measuring the boundary of the droplet and the background to obtain a characteristic length scale of the droplet, e.g. radius and/or diameter. Another preferred option is to determine the integral area of the droplet, e.g. the number of pixels.

As set out above, an advantage of using machine vision resides in the fact that machine vision is relatively independent of the bulk properties of the liquid in the droplet. This is particularly beneficial where during the total duration of the process, changes in the liquid composition may occur as for instance in a 'gradient-run' in liquid chromatography. During a gradient run, a mixture of two or more solvents, which is used as the eluent, is changed during time. For instance a chromatographic run may start at a ratio of 10% wt. water to 90% wt. methanol blend, and may change over a time period to 100% wt. water and 0% wt. methanol. Such a gradient run is common in analytical applications where it is used to decrease chromatographic run time.

Independently of whether a closed or open system is employed, in step a) a droplet is formed. This is achieved by passing the fluid sample through the lumen of the tubular vessel until the droplet is formed at the distal end of the tubular vessel. The droplet will have a first defined volume, which corresponds to a defined surface area, and, at a given geometry to a defined diameter.

The droplet may thus be defined by its diameter, surface area and/or volume, all of which are functions of the surface tension at the gas/liquid boundary, and of the shape of the tubular vessel.

If a droplet is supposed to be transferred to a receiving means, or if a droplet is supposed to be disposed off, the droplet preferably is a pendant, i.e. freely-hanging droplet, balanced by the equilibrium between upward tubular vessel and surface forces and downward gravitational forces. Droplets of up to 5 µL volume have been shown to successfully hang at a tubular vessel exit before gravitational forces become larger than the upward forces.

However, the droplet may have a different, smaller volume. Preferably the droplet comprises of from 0.001 to 15.0 µL, more preferably of from 0.01 to 14.0 µL, yet more preferably of from 0.1 to 5.0 µL of liquid feed.

If the droplet is a pendant droplet, it will usually have a diameter of less than 500 µm diameter. The volume and the diameter are linked by a cubic function relative to the diameter: while a droplet with a 50 µm diameter represents a volume of 65 picoliters, a 500 µm diameter drop represents in 65 nanoliters volume.

The droplet may have a spherical shape or a meniscus shape, or an elongated droplet sheet shape, or any shape between the three. The spherical shape is most preferred, since it has the advantage that when evaporating the solvent in a spherical droplet, the surface to liquid volume ratio is maximally increased, maximizing the evaporation rate, whilst minimizing analyte adsorption. In any case, if the boundaries are known such as the size of the tubular vessel, the diameter and shape, and hence the volume of a droplet may advantageously be determined from the diameter and shape of a droplet.

In a preferred embodiment, the pendant droplet volume is kept constant and gradient runs are performed automatically. This greatly reduces the solvent evaporation parameter complexity. In this case, the droplet size may preferably be continuously maintained, in the so-called constant droplet size mode.

If the volume or evaporation rate of the solvent blend is changing through the process, e.g. at a solvent gradient, the droplet volume is preferably continuously monitored.

While this may be performed by all suitable optical means, such as a photodiode and laser or focused light beam set-up, due the difference in droplet shape that may occur in a single run, the monitoring is preferably performed via a machine vision setup that is coupled to a heater/gas flow unit in a feedback modus, the heater/gas flow unit providing the defined gas flow.

The device according to the invention further preferably comprises a means for dispensing the droplet from the distal end or within the lumen of the tubular vessel.

The device according to the invention further preferably may comprise a means (c) for diluting the concentrated sample droplet in a second solvent or solvent blend to obtain a re-diluted sample.

The present invention further relates to an arrangement for the multi-dimensional separation of a liquid feed comprising one or more components wherein the device is employed. The arrangement preferably comprises i) at least a first separation device for the separation of components diluted in a first solvent or solvent blend in a first dimension into a first liquid feed; and ii) a device according to the invention for selective solvent evaporation from the first liquid feed to obtain one or more concentrated droplets, and iii) a device for analysing the components in the concentrated droplets. Preferably, the device for analysing the components in the concentrated droplets may comprise a physical and/or chemical analysis tool. This allows to integrate the separation method directly with a suitable analysis tool, which is highly desirable for instance for analytical devices typically employed in medical laboratories that perform serial analysis.

The present invention further relates to a process for the selective solvent removal from a liquid feed comprising one or more components diluted in at least a first solvent or a solvent blend, as set out above.

In this process, the droplet preferably has a defined volume, with a first defined surface area.

The present process preferably separates components that are less volatile than the solvents employed.

Components that have a higher vapour pressure than one or more of the solvents, will likely be removed at least in part during the evaporation step. These can however be advantageously retained in the effluent gas flow, for instance by installing a cold trap. Furthermore, the presence of such components can be monitored indirectly through a change in the required heating power, which can indicate the presence of such components. This is beneficial since it indicates reliably the presence of low boiling components that may require a different determination method.

The process is preferably continuously adjusted, by means of measuring various parameters, such as volume, shape, effluent gas composition, effluent gas flow rate, temperature and/or pressure, and adjusting one or more parameters of the device that control the evaporation and/or inflow rate.

The influence of the presence of lighter components on evaporation and accumulation rate is considered initially not relevant since the components are present in a dilute form and hence will only influence the rates to a negligible extent.

Advantageously, in the process, the evaporation rate $r_2$ is equal or higher to the flow of liquid feed $r_1$ added to the droplet through the tubular vessel. As a result, the contents of the droplet becomes more concentrated over time, which allows e.g. to operate at a higher concentration for a second separation process, resulting in more sensitive analyses.

In a particularly preferred way of executing the present process, the defined droplet volume is essentially kept constant.

While there are many suitable ways known to a skilled person to sense the droplet surface area, a particularly advantageous way is by monitoring the defined droplet surface area by machine vision, as set out herein below.

The present process may be operated in an open or in a closed set-up. In a closed system, i.e. a system that is closed with respect to gas flow and without pendant droplet, in order to control the evaporation process, the mass, volume or mole flows in the system may advantageously be determined and controlled by measurement of geometrical parameters of the fluid meniscus.

Preferably, the vessel in such a closed system is transparent in a wavelength region that allows measurement of the geometrical parameters of the meniscus to be performed, e.g. made from glass or suitable transparent polymeric materials for optical measurements, or silicon for infrared measurements.

The liquid feed preferably is subjected to a first separation through CE and LC (RP, NP), the latter eventually coupled with a suitable detector indicating presence of components and/or solvents in an aliquot of the liquid feed as set out below Upon formation of a suitable concentrated droplet, or a re-dissolved droplet, the concentrated droplet may preferably be dispensed from the tubular vessel. The thus dispensed sample may advantageously be re-dissolved in a second solvent or solvent blend where required by a second stage. The re-dissolved sample may then advantageously serve as liquid feed for a second separation process. Alternatively, the concentrated droplet may also be redissolved immediately prior to being dispensed, e.g. if the droplet was formed inside a tubular vessel rather than at its tip, or by supplying the second solvent or solvent blend to the concentrated droplet at the tip.

The concentrated droplet may however also be subjected directly to a further separation of analysis step without addition of a second solvent or second solvent blend, e.g. when using the concentrated droplet for mass spectroscopy.

After evaporation, the droplet is preferably periodically transferred into a droplet sample reservoir which can be switched to a secondary liquid feed.

In a preferred embodiment, the droplet is transferred to and released through the droplet receiver into a sample reservoir for redissolving in the second solvent, or re-dissolved by other suitable means for adding the second solvent before introducing it into the sample reservoir.

The tubular vessel may comprise an ejection actuator that may effect a shock wave ejecting the droplets out of the liquid surface. However, it was found that in particular concentrated small droplets are difficult to eject with a predictable trajectory.

The tubular vessel may yet more preferably further comprise several layers, wherein one or more capillaries may be located close to the tip, e.g. concentrically around the tip of the ejection tube, where the droplet or a meniscus of dispensing liquid develops which extends beyond the tip of the ejection tube. Preferably, the outermost tubular protrudes beyond the inner capillaries in the direction of a longitudinal axis of the ejection tubular vessel.

Preferably, at least parts of the surfaces of the ejection tubular wall are hydrophilic. More preferably, at least an outer surface of the tubular vessel is hydrophobic, yet more preferably through treatment or material choice, e.g. treatment with a silane such as hexamethyldisilazane.

Preferably, the tubular vessel is shaped such that there is a sharp edge between the hydrophilic interior surface side and the hydrophobic exterior surface of the outermost tubular vessel, for instance by shaping the distal end such that no or hardly any wetting by the solvent or eluent can occur at the outside, thereby minimizing the contact angle by design and/or material choice.

In step b), the droplet is subjected to an evaporation process at a defined evaporation rate. This may advantageously be performed by contacting the droplet with a defined gas flow of a carrier gas, and/or by applying under-pressure, by placing a heating unit into close proximity of the droplet, and/or any combination of these. A heating unit according to the subject invention should be understood as any means providing heat or heated gas flows, either through convection, radiation or other means. In this step, at least part of the first solvent or solvent blend present in the droplet is removed at least in part from the sample, by evaporation, i.e. by boiling off or by sublimation.

The device according to the invention further preferably comprises a means for dispensing the droplet from the distal end or within the lumen of the tubular vessel.

The device according to the invention further preferably may comprise a means for diluting the concentrated sample droplet in a second solvent or solvent blend to obtain a re-diluted sample.

The present invention further relates to an arrangement for the multi-dimensional separation of a liquid feed comprising one or more components wherein the device is employed. The arrangement preferably comprises i) at least a first separation device for the separation of components diluted in a first solvent or solvent blend in a first dimension into a first liquid feed; and ii) a device according to the invention for selective solvent evaporation from the first liquid feed to obtain one or more concentrated droplets, and iii) a device for analysing the components in the concentrated droplets. The present invention further relates to a process for the selective solvent removal from a liquid feed comprising one or more components diluted in at least a first solvent or a solvent blend, as set out above.

In this process, the droplet preferably has a defined volume, with a first defined surface area.

The present process may be operated in an open or in a closed set-up. In a closed system, i.e. a system that is closed with respect to gas flow and without pendant droplet, in order to control the evaporation process, the mass, volume or mole flows in the system may advantageously be determined and controlled by measurement of geometrical parameters of the fluid meniscus. Preferably, the vessel in such closed system is transparent in a wavelength region that allows measurement of the geometrical parameters of the meniscus is performed, e.g. made from glass or Perspex for optical measurements, or silicon for infrared measurements.

The liquid feed preferably is subjected to a first separation through CE and LC (RP, NP), the latter eventually coupled with a suitable detector indicating presence of components and/or solvents in an aliquot of the liquid feed as set out below.

As a result of the subject process, a concentrated sample is obtained, either neat or in a solvent remnant. The solvent blend in the droplet may change during this process, e.g. by azeotropes formed, thereby resulting in a solvent gradient over time.

This concentrated sample is then preferably diluted with a second solvent or solvent blend, to obtain a re-dissolved sample.

The re-dissolved sample droplet is then preferably transferred into a sample receiving means for receiving an aliquot of the fluid re-dissolved sample. Step c) may preferably be combined with this transfer step.

Preferably, the device according to the invention comprises an embodiment for droplet release for transport to, or insertion into a subsequent separation or detector instrument.

The first tubular vessel is preferably attached to a translation means through which the re-dissolved droplet can be brought to or into contact with said receiving unit. In the case of a pendant droplet, the receiving means is preferably positioned underneath the tubular vessel and/or the droplet, such that a released droplet falls into said receiving unit through gravity.

More preferably, the droplet release from the first tubular vessel is achieved by applying mechanical or electrical force, including through a piezoelectric element, a shape memory alloy, a magnetostrictive element, and/or an electrode capable of applying an electrostatic field; a gas pulse, laser pulse, knife, hydrostatic shock, electrostatic shock, wicking, capillary action, and/or differential pressure.

The droplet receiver and linked reservoir may be a second tubular vessel whereby the droplet may be transferred through coalescence, the droplet may be received by a cup-shaped droplet receiver linked to a reservoir, which preferably may be assisted by suction; by coalescence with a second droplet of the second solvent.

The droplet receiver is then preferably connected to a second tubular vessel for sequential analysis and separation, which may advantageously include a valve or fluid switch for adding solvent to this sample volume, as disclosed in Hongzhe Tian et al. as described herein-above.

Preferably, in the apparatus according to the invention, the first tubular vessel means may represent the outlet of a first chromatographic separation unit, wherein the unit may consist of a chromatography column, a solid-phase extraction column and/or the outlet of an electrophoresis column. More preferably, the first tubular vessel may be directly connected to the inlet of a detector, such as a UV detector, and/or fluorescence detector.

The receiving means preferably comprises a receiving surface, preferably shaped as a well, reservoir, tube, channel, tubular vessel or inlet.

More preferably, the apparatus comprises at least a first receiving device with a plurality of receiving units that may receive a plurality of droplets.

Preferably, this droplet receiver may further comprise a translation means to which a receiving unit is attached, such as to receive sample droplet. The translation means may comprise, preferably, a MALDI plate, a multiwell plate, a hybridization plate and/or a Lab-on-a-Chip.

The re-dissolved sample may also be preferably introduced into a second separation and/or analytical method, such as, but not limited to separation and/or analytical techniques including LC such as RP, NP, TLC; CE, NMR, MS, UV/VIS, nano LC, HPLC, UPLC; RP-(UV/VIS)-EV-NP-MS; RP-(UV/VIS)-EV-NMR; NP-(UV/VIS)-EV-CE-MS/RP-(UV/VIS)-EV-CE-MS; RP(UV/VIS)-EV-TLC/NP-(UV/VIS)-EV-TLC; EV-nano LC and CE-EV.

The droplet receiver line-up further preferably comprises a valve, wherein the reservoir may form part of the inlet of the valve in which the droplet is released. Then the valve facilitates transfer of the sample to a subsequent separation or detector instrument.

In an alternative embodiment of the subject device, the droplet receiver is part of the tubular vessel, wherein the flow is reversed once the droplet has been concentrated to a desired volume. The concentrated droplet may be drawn back into the capillary lumen of the tubular vessel, by applying a reduced pressure, and subsequently sent to a different conduit through a switch valve towards a separate analysis process or separation process.

This is preferably attained by a device further including a valve or fluid switch in fluid communication with the tubular vessel lumen, and at least a translation conduit in communication with the valve for adding solvent to this sample volume.

Accordingly the present invention also relates to a device for selective solvent evaporation from a liquid feed, the feed comprising one or more components diluted in at least a first solvent or a solvent blend, comprising:

a) A first tubular vessel having a distal end or a channel suitable for the formation of a droplet of a first volume, at an inflow rate $r_1$, at the tip or in the lumen of the tubular vessel, and b) means for subjecting the droplet to a solvent evaporation step at an evaporation rate $r_2$ to evaporate at least part of the first solvent or solvent blend, and to accumulate the components in the feed in the droplet during the evaporation process at an accumulation rate $r_3$, to obtain a concentrated feed volume in the droplet, and c) A means for drawing the concentrated droplet back into the channel of the first tubular vessel, and translating the droplet into a translation conduit for further analysis or separation.

The means for drawing the concentrated droplet back into the channel of the first tubular vessel may comprise a metering device, such as a syringe comprising a plunger and a cylinder, to draw up a desired volume by moving the plunger back a certain distance, thus drawing the fluid of the concentrated droplet into the lumen of the tubular vessel. The fluid is then preferably drawn through a valve into a reservoir, from where it may be translated to a further step for further analysis or separation.

Alternatively, the droplet receiver and the tip of the tubular vessel may form a relatively pressure-tight fluid communicable connection so that the droplet volume may then be injected into the droplet receiver.

The present invention also relates to an apparatus for use in automated fluid processing, comprising a plate having a structure integrated therein including at least one inlet in fluid communication with at least one outlet, each of the at least one inlet and the at least one outlet connectable in a relatively pressure-tight fluid communicable connection with one of the plurality of transport connectors so as to form an enclosed fluid pathway through the structure; and at least one reservoir disposed downstream from the first inlet and upstream from the first outlet such that a fluid injected through the first inlet traverses the at least one reservoir prior to transport to the first outlet.

The apparatus also preferably comprises a means for waste liquid disposal, such as a tube, well or absorbent material to which a droplet can be transferred that is not of interest for further analysis.

The heating means preferably comprises a heat-source for heating up the gas around the droplet, or an irradiation unit that is heating up the droplet directly. Also a heating means may preferably be present which is used to pre-heat the solvent going into the droplet. In the case of a capillary vessel with a distal end holding a droplet, a heating element is preferably positioned around the capillary vessel to heat the internal liquid feed.

Preferably the droplet or meniscus is enclosed in a partially enclosed chamber that assures laminar air-flow along the droplet to enclose the heated space and assures removal of evaporated compounds. This partially enclosed chamber preferably has a bell shape or (frustro) conical shape with a continuous reducing radius, wherein an opening is arranged on an upper part to assure outlet of gas and an opening on lower part to assure transfer of the droplet for downstream processing and fresh gas influx.

Preferably, the heater comprises one or more coils, wires or patterned metal lines on a substrate, which more preferably are positioned such that transfer of the droplet to a next channel, surface, well, reservoir, tube, tubular vessel or inlet is facilitated.

The droplet receiver also may be preferably connected to a second tubular vessel placed in the direct vicinity of said first tubular vessel, such that the droplet can be brought into contact with a second droplet, containing eluent of different or same composition as eluent in the eluate coming from said first tubular vessel.

In a preferred embodiment, the droplet size is continuously monitored by a machine vision setup that is coupled to the heater in feedback modus. In this way, droplet size and evaporation rate is controlled and monitored to match the eluent feed rate of the primary column. The evaporated sample volume is kept constant and gradient runs are performed automatically.

In a preferred embodiment of the present process, the pendant droplet size is monitored continuously by a machine vision setup that is coupled to the heater in feedback modus. In this way, droplet size and evaporation rate are controlled and monitored to match any isocratic or gradient eluent feed of the primary column.

This preferred setup may be used in a constant droplet-size mode, preventing dry-cooking of the sample.

After evaporation, the droplet may be transferred to and released into a vial, e.g. one that contains 100 µL deuterated NMR solvent for subsequent NMR analysis.

Alternatively, after evaporation, in a preferred embodiment, the droplet may be transferred to and released into a sample reservoir in fluid communication with the droplet receiver, which is part of a valve, or connected to a valve.

The valve preferably has a dedicated design to suit small droplet volumes (e.g. 50-500 nL), whereby these volumes are 25-100 times smaller as those reported in prior art. As a result, it is expected that even a remainder of solvent in the droplet would not deteriorate the chromatographic separation, due to reduced solubility problems, less interference towards stationary phase and other effects.

The sample reservoir preferably may also enable accurate and constant injection volumes which due to the small dimensions decrease the peak band broadening effects as well as enables the transition between low and high pressure region, e.g. 1 and 200 bar, which is needed to perform a fast second separation step. A fast second dimension separation is preferably applied because the preferably the first dimension separation is not halted. Halting the first dimension separation will lead to band dispersion and a significant reduction in the quality of the first dimension separation. The subject process therefore preferably operates at a concentration of components whereby the solvent evaporation rate remains predominant.

Preferably the process operates under conditions whereby more than 75% of the overall evaporation rate is contributed by the solvent or solvent blend.

The subject device and process may advantageously be employed in separations followed by a bioassay, such as an immuno assay or enzyme assay. Since in these assays the components and kit components (e.g. reaction vessels) are usually sensitive to solvents, it is preferred that essentially any inhibiting solvent is removed from the concentrated droplet prior to the assay.

The following, non-limiting experiments illustrate a preferred embodiment of the present invention.

Experiments:

Droplet sampling using Machine vision controlled evaporation: A machine vision control loop was developed with (LabVIEW 2010 f2, NI DAQmx device drivers 9.2.2 and additional machine vision and PID control loop package). A Basler A601f camera was installed on a Proximity Infinitube and equipped with a M-plane Apo 2× Mitutoyo objective to obtain images (28 fps). A NI-cDAQ 9172 module with NI 9264 voltage output module was used to convert the PID output via a linear power thyristor into heat by a heated gas gun. A Luxeon power LED (wattage and lumen) was used as backlight to produce a droplet silhouette to enhance edge detection.

The droplet sampling system comprised of a stainless steel tubing (20 cm long, 1/16" OD and 0.125 mm ID) which was connected to a fused silica capillary (20 cm 0.36 mm OD and 0.1 mm ID) which was connected to a switching valve (RheodyneMX series II model MXT 715-102). The switching valve was equipped with a 10 µL loop and connected to a syringe pump (RS-232 remotely controlled Harvard pump model 22).

The pump was used to draw droplet fractions with a flow speed of 35 µL min$^{-1}$. A steppermotor was used as means to move the receptacle from the flush reservoir towards the droplet and back. The droplets were transferred into the loop in approximately 15 seconds. The sampling duration was set to a 180 s per cycle.

LC system: A Dionex Ultimate 3000 HPLC system (FLM 3×00 Flow Manager, LPG-3×00 pump, LC Packings UVD-3000 Detector, WPS-3000 autosampler) was used to supply a HILIC (Phenomenex Luna 3 µm HILIC 200 Å Length 150 mm and ID 2.0 mm) and a RPLC column (Varian C18 column 150 mm 2 mm ID) of eluent. For the two-dimensional evaporation LC runs, an isocratic HILIC method based on 90% ACN 10% Ammonium Formate buffer (100 mM) with a flow of 20 µL min$^{-1}$.

Stock solutions: Seven stock solutions containing single analytes were prepared in 50% methanol and 50% water solutions. From each stock solution, 50 µL was pipetted into a 1.5 mL vial (brand) and 1.2 mL of acetonitrile was added (see Table 1).

TABLE 1

| Substance | Stock concentration (50/50 MeOH/H2O) g/mL | Volume pipette µL | Concentration in sample mix (11% MeOH, 11% H2O & 78% ACN) µg/mL |
|---|---|---|---|
| Methyl paraben | 0.98 | 50 | 31.61 |
| Ethyl paraben | 1.37 | 50 | 44.19 |
| Propyl paraben | 1.00 | 50 | 32.26 |
| Uracil | 0.99 | 50 | 31.94 |
| Adenine | 1.19 | 50 | 38.39 |
| Adenosine | 1.50 | 50 | 48.39 |
| Cytosine | 1.45 | 50 | 46.77 |

Setup of the evaporation system: The evaporation setup comprised of a Harvard pump (model 22) delivering a 5 µL min-1 flow of solvent through a fused silica capillary (length 70 cm, ID 100 µm, OD 365 µm) which is coupled to a stainless steel capillary (length 15 cm, ID 100 µm, OD 1.57 mm). When operating, a droplet emerged at the distal end of the capillary and was freely hanging, balanced by the equilibrium between upward capillary and downward gravitational forces. The width of the droplet was monitored by long distance microscope optics coupled to a CCD image sensor (Proximity Infinitube & Basler A601f).

As versatile control mechanism for evaporating LC effluent under changing system parameters (e.g. solvent composition, flow speed, ambient changes etc.) machine vision was employed.

Characterization of the droplet evaporation system: It was found that thee combination of machine vision and the PID control loop was very powerful because it enabled a relatively easy and versatile automated process control. Within the physicochemical limits, the setup handles various LC eluent flowrates for isocratic, yet more importantly, of gradient solvent systems. A large advantage is obtained here since a wide variety of column types and elution programs be used without the need of extensive knowledge of solvent properties and system parameters.

Figure 5:
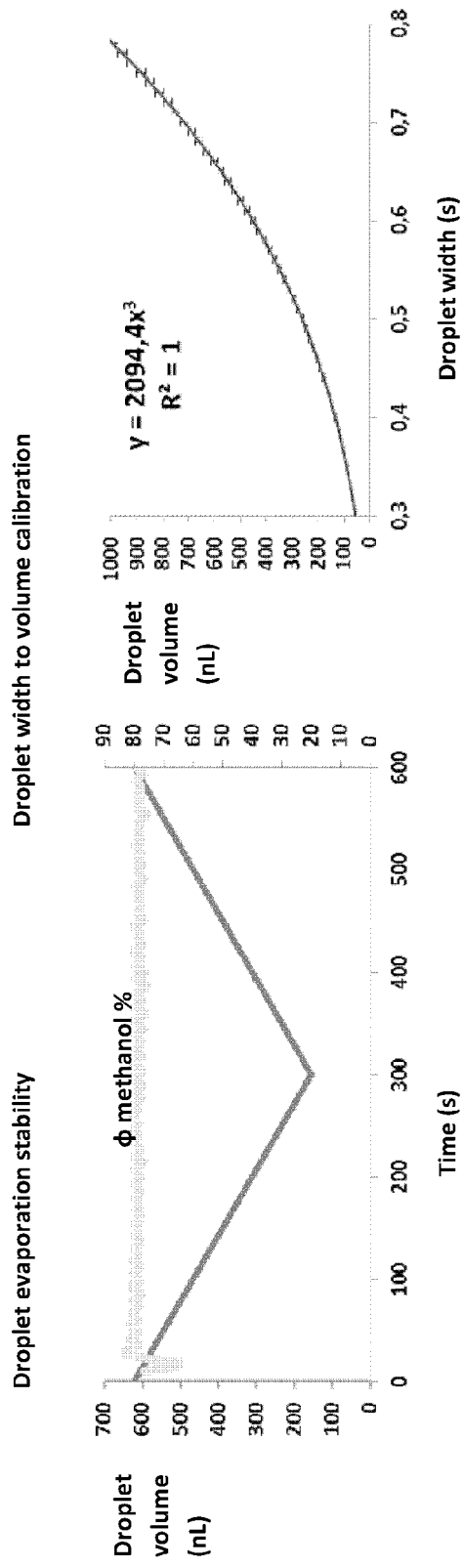
FIG. 5 shows plots of droplet evaporation stability over time, and Droplet width to volume calibration.

The droplet evaporation interface was characterized by measuring the droplet size under changing solvent composition. FIG. 5 shows the stability of a droplet while the eluental composition is changed during a gradient run. In FIG. 5, the droplet stability (blue line) during evaporation of an LC gradient (red line) ranging from 80% to 20% methanol/water composition at 20 µL min-1 flow is shown. After 40 s equilibration time, the evaporation process becomes stable. Flow rates up to 60 µL min-1 have been handled but mark the physical limit of the current prototype.

Because the pendant droplet is not perfectly hemispherical but rather is a stretched out version of a droplet due to gravitational forces, the droplet volume cannot be accurately calculated. A more precise determination was achieved by plotting a known droplet volume (at a certain time interval) to the measured droplet width. The deduced droplet volume was based on an accurate flow rate and time interval. Since a pendant droplet will typically not be perfectly hemispherical but rather a stretched out version of a droplet due to gravitational forces, the droplet volume can only ba approximately calculated.

A more precise determination was achieved by plotting a known droplet volume (at a certain time interval) to the measured droplet width. The deduced droplet volume was based on an accurate flow rate and time interval (see FIG. 5).

Figure 6:
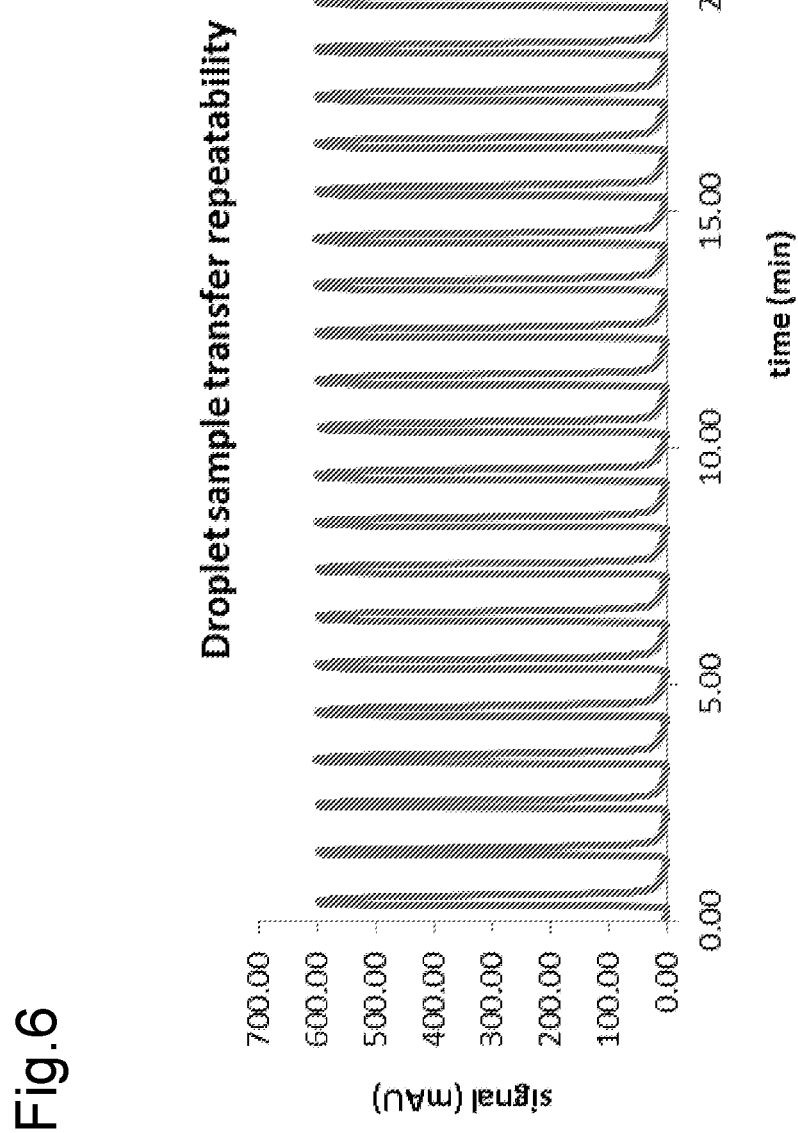
FIG. 6 illustrates the droplet sample repeatability, whereby the recovery of the droplet transfer system was assessed by comparing peak areas obtained by 1 μL autosampler injections (38.4±1% μg/mL adenosine solution n=5) to 1 μL receptacle injections. The droplets were transported into a sample loop through application of reduced pressure.
Figure 7:
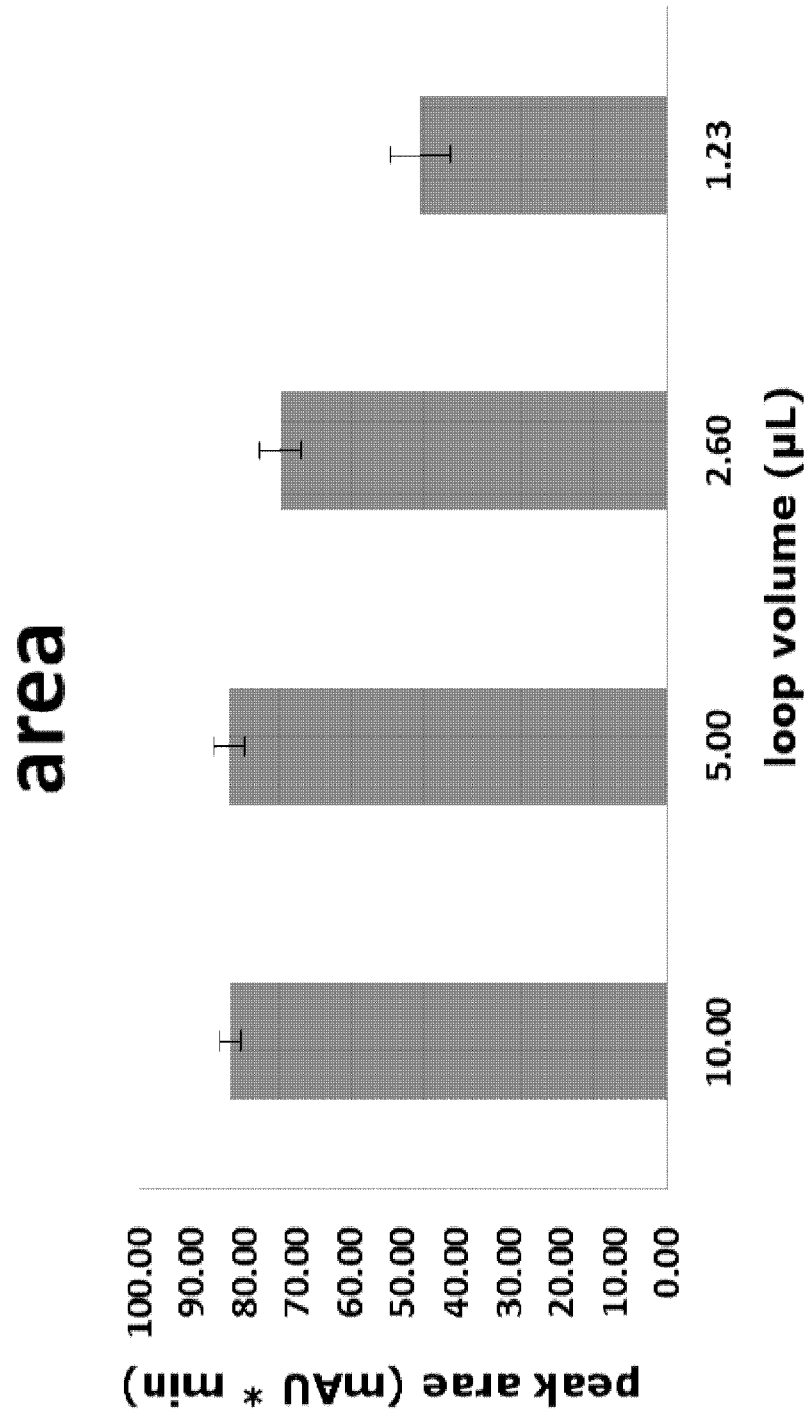
FIG. 7 shows the optimal sample loop size, determined through several injection of 1 μL adenosine containing droplets, at 1 μL droplet volumes (n=15, adenine sample) for respectively a 10.0, 5.0, 2.6 and 1.2 μL injection loop volume.

Recovery of receptacle sampling, repeatability of transfer and the concentration effect of droplets: Experiments were performed to assess the capabilities of the droplet sample transfer system in terms of the droplet receptacle sampling recovery, droplet sampling repeatability, and the droplet concentrative effect (see FIG. 6). The recovery of the droplet transfer system was assessed by comparing peak areas obtained by 1 µL auto sampler injections (38.4±1% µg/mL adenosine solution n=5) to 1 µL receptacle injections, as set out in FIG. 6. The droplets were transported into a sample loop through under pressure, i.e. reduced pressure with respect to the ambient pressure. Recovery of droplet receptacle sampling: The recovery of the droplet transfer system was assessed by comparing peak areas obtained by 1 µL auto sampler injections (38.4±1% µg/mL adenosine solution n=5) to 1 µL receptacle injections see FIG. 7. The droplets were transported into a sample loop through reduced pressure (under pressure as compared to the pressure in the environment.

Optimal sample loop volume: Due to peakband broadening effects, the loop size is most often chosen larger than the initially injected volume, to ensure all sample material is transferred. However, the larger the sample loop volume is, the larger the solvent incompatibility issues are regarding an orthogonal secondary separation column.

Therefore, a preferred minimal sample loop volume for safely injecting 1 µL droplet volumes was determined. Satisfactory recoveries were obtained for a 10 µL loop (100%±1.99%) and a 5 µL loop (100%±2.89%). Smaller sample loop volumes mounted in decreased recoveries. For a 2.6 µL sample loop, the recovery is 89%±3.91% and for a 1.2 µL loop 57%±5.61% (see FIG. 7).

Figure 8:
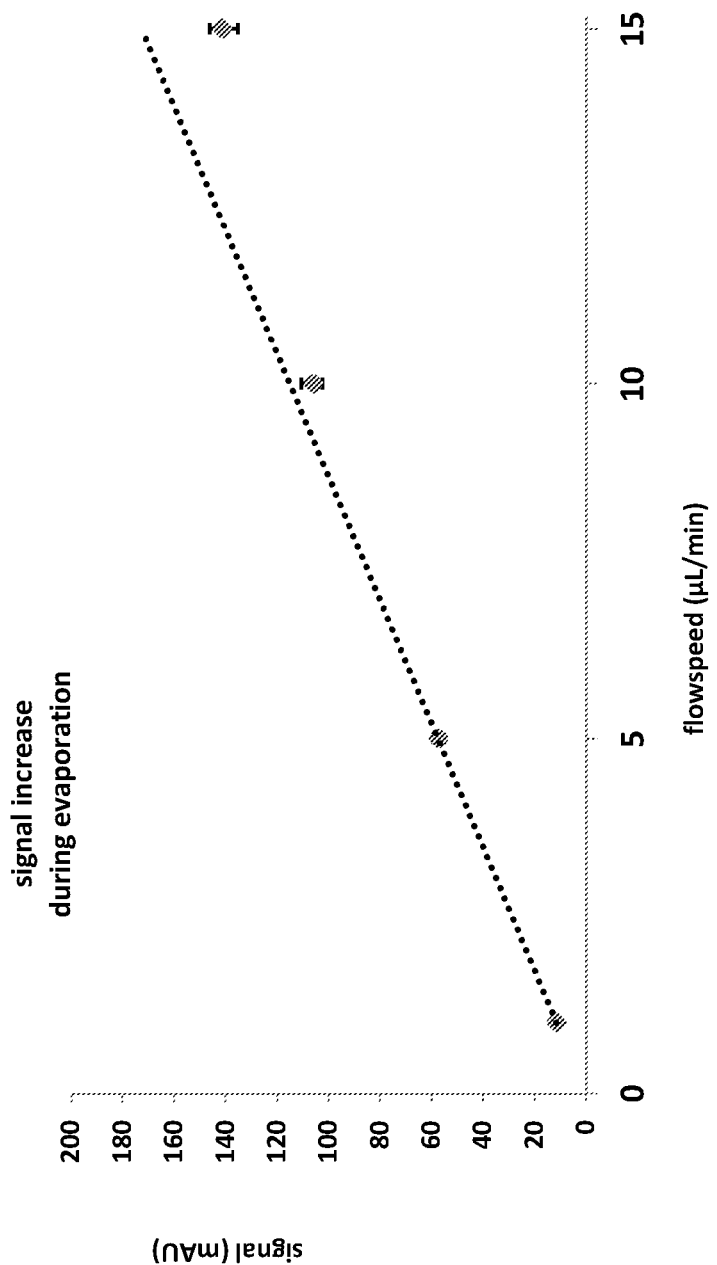
FIG. 8 illustrates the signal increased during evaporation, as illustrated by The effect of evaporation on the signal intensity of an adenine sample solution obtained for 500 nL droplet sample injections for different feed rates.

FIG. 8 illustrates an added advantage of the evaporation interface, i.e. the concentrative effect. This effectively means that analyte enriched and sub-µL volumes can now be injected into the next separation dimension. The combination of both is highly beneficial for decreasing solvent incompatibilities, in particular for orthogonal LCxLC systems, yet realizing an increase in sensitivity. FIG. 8 shows the concentration increases that were obtained for 1 minute evaporation intervals at incremented flow speeds. The dotted trend line shows the maximal theoretical increase in concentration and the blue dots the experimental obtained signals (n=6).

Figure 9:
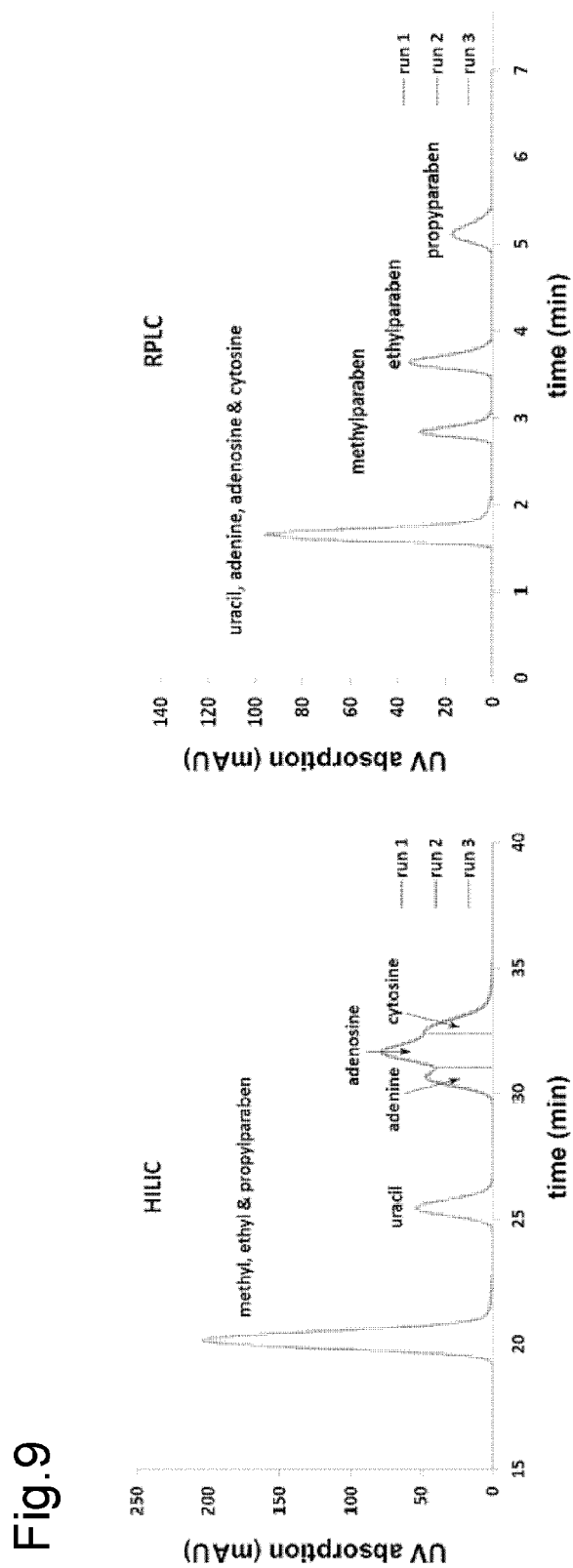
FIG. 9 illustrates the performance of conventional LCxLC was compared with LC-EV-LC by the separation of a test sample mixture under identical chromatographic settings.
Figure 10:
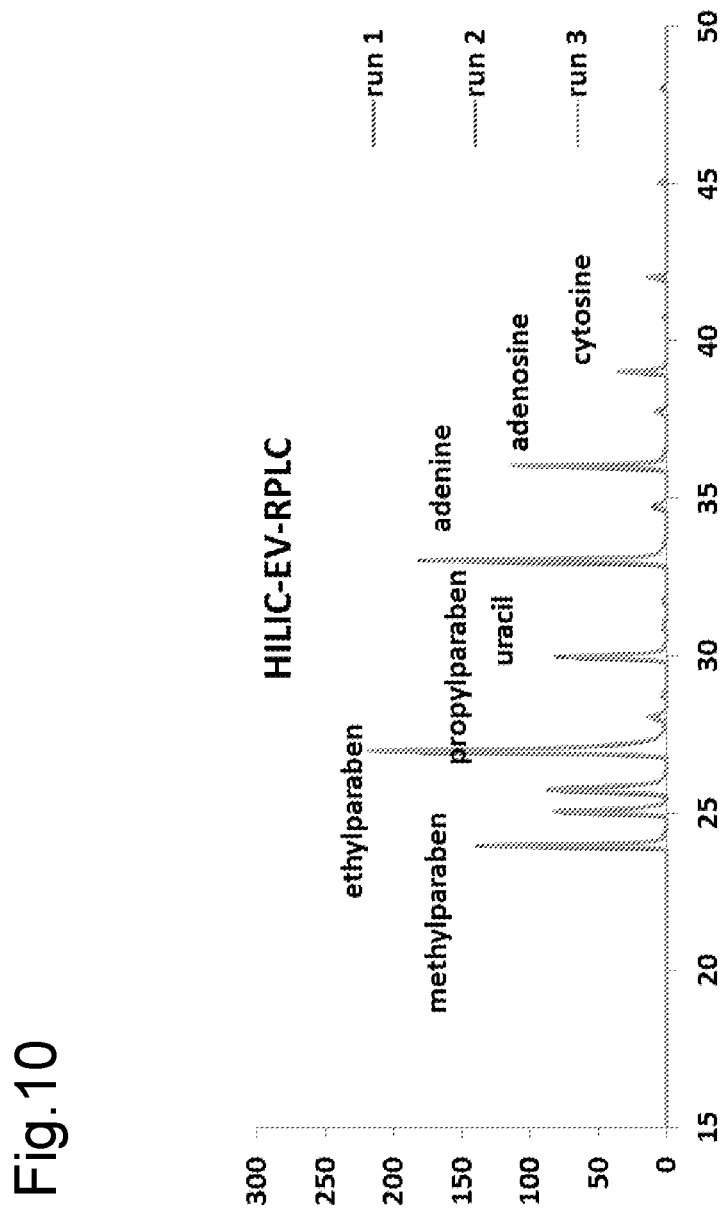
FIG. 10 shows the advantages of LC-EV-LC over conventional LCxLC. The chromatographic settings, especially the modulation time were kept identical to obtain a good comparison in performance.

FIGS. 9 and 10 show how conventional LCxLC compares to LC-EV-LC: The performance of conventional LCxLC was compared with LC-EV-LC by the separation of an academic sample mixture under identical chromatographic settings. In this section we compare the results of uni-dimensional HILIC and RPLC approach, conventional LCxLC and the LC-EV-LC approach. Uni-dimensional Hilic: HILIC is a technique for the separation of semi-polar to polar compounds. Nonpolar compounds are thus unretained. For the test mixture, the first peak composes of three nonpolar analytes (methyl, ethyl and propyl paraben). In the case of a complex sample mixture, clearly the separation power of a unidimensional HILIC approach is insufficient especially for the nonpolar molecules, at injection volumes of 1 µL, 20% buffer 200 mM AmFor, 80% ACN, 20 µL min-1, mix 7 components (see FIG. 9, left spectrum). The same counts for the RPLC separation approach. Now the non-polar compounds are separated well but the nonpolar compounds are unretained and elute the column disguising even as a single peak (see FIG. 9, right spectrum). FIG. 10 then clearly illustrates the advantage of LC-EV-LC over conventional LCxLC. The chromatographic settings, especially the modulation time were kept identical to obtain a good comparison in performance.

Figure 11:
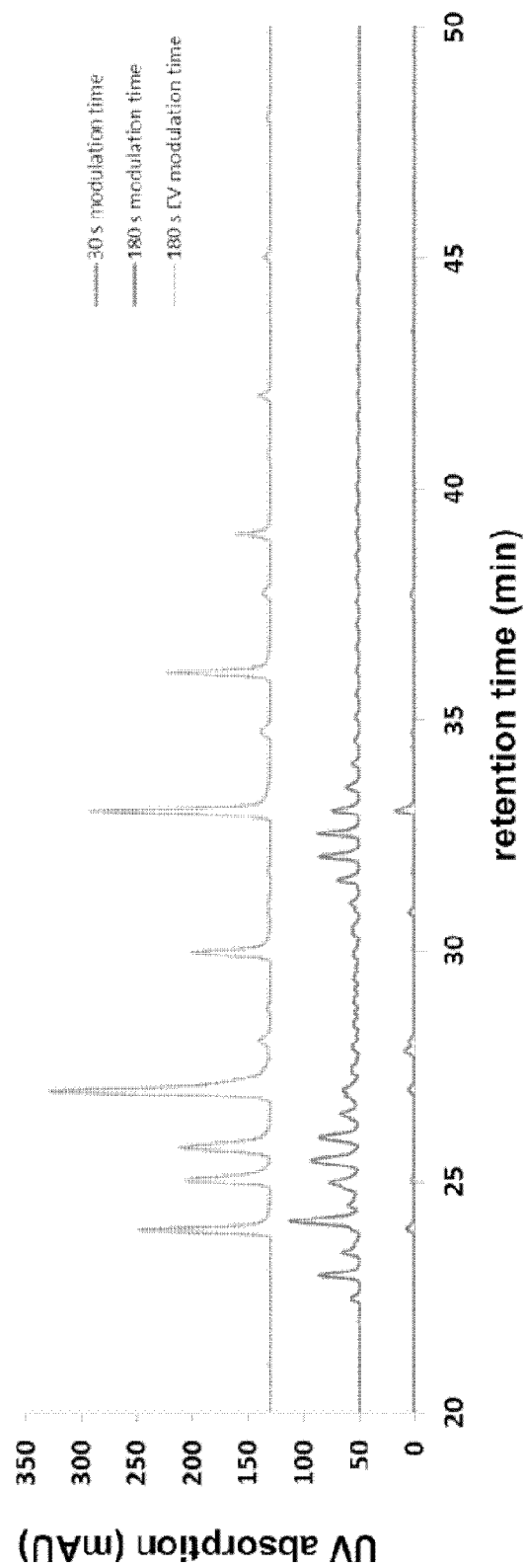
FIG. 11 shows the same mixture when using different modulation times of 180 s, LCXLC, 30 s LCxLC, and 180 s LCxEVxLC from bottom to top, allowing to avoid overload of the columns and loss of the analyte.

Modulation times: when using an injection loop of 10 µL, the modulation time of 3 minutes combined with a flow of 20 µL min$^{-1}$ for the HILIC imposes that analyte material is lost. FIG. 11 shows the conventional LCxLC approaches faces the chromatographer with a trade-off, overload column and decrease separation quality or under-load the column and decrease peak heights, while shorter modulations lead to loss of analyte. This issue is resolved by the current receiver and methods, see the overlay of spectra in FIG. 11.

The above results indicate that the receiver, and apparatus and methods wherein it used will result in better resolution, and cleaner chromatograms and increased peak heights, as well as an increased time for second dimension resolution.

The invention claimed is:

1. A droplet receiver comprising:
a receptacle for receiving a droplet;
a fluid conduit connected at a first end thereof to the droplet receptacle, thereby providing a course within which the droplet received in the droplet receptacle can move, the fluid conduit being at its distal end in fluid communication with a reservoir;
a fluid layer wetting the internal walls of the receptacle and conduit in such a way as to permit reception of the droplet without loss of the received droplet due to wetting of the internal receptacle and conduit walls; and
a pressure reduction unit configured to apply a reduced pressure to draw the received droplet into the reservoir.

2. The droplet receiver according to claim 1, wherein the reservoir further comprises a wetting unit configured to wet the internal receptacle and conduit walls.

3. The droplet receiver according to claim 1, wherein the droplet receiver is mounted on a support movable at least in an upward and downward direction, and wherein the uppermost position permits to contact a pendant droplet.

4. The droplet receiver according to claim 1, wherein the fluid layer is a liquid layer exhibiting a flow.

5. The droplet receiver according to claim 1, further comprising a fluid feeding unit.

6. The droplet receiver according to claim 5, wherein the fluid feeding unit comprises a fluid bath for submerging the receptacle when not receiving a droplet.

7. The droplet receiver according to claim 6, further comprising a valve at the reservoir and a second conduit in fluid communication with the valve, to direct a plug flow of a received droplet to a further analysis or separation process.

8. The droplet receiver of claim 7, wherein the reservoir comprises a fluid overflow conduit for reverting fluid back to the fluid feed.

9. The droplet receiver according to claim 6, wherein the fluid bath is provided with an inlet and an outlet for the circulation of the fluid.

10. The droplet receiver according to claim 1, wherein the internal space of the receptacle is shaped such that a sectional area thereof is reduced towards the conduit.

11. A device for selective solvent evaporation from a liquid feed, the feed comprising one or more components diluted in at least a first solvent or a solvent blend, the device comprising:
a first tubular vessel having a distal end or a channel suitable for the formation of a droplet of a first volume, at an inflow rate $r_1$, at the tip or in the lumen of the first tubular vessel;
a heating unit configured to subject the droplet to solvent evaporation at an evaporation rate $r_2$ to evaporate at least part of the first solvent or solvent blend, and to accumulate the components in the feed in the droplet during the evaporation process at an accumulation rate $r_3$, to obtain a concentrated feed volume in the droplet; and
comprising a receptacle for receiving the droplet, a fluid conduit connected at a first end thereof to the droplet receptacle, thereby providing a course within which the droplet received in the droplet receptacle can move, the fluid conduit being at its distal end in fluid communication with a reservoir, a fluid layer wetting the internal walls of the receptacle and conduit in such a way as to permit reception of the droplet without loss of the received droplet due to wetting of the internal receptacle and conduit walls, and a pressure reduction unit configured to apply a reduced pressure to draw the received droplet into the reservoir.

12. The device according to claim 11, wherein the device comprises an adjustment unit configured to adjust one or more of pressure, temperature and gas flow rate at the gas/liquid interface of the droplet.

13. The device according to claim 11, further comprising: an automated system configured to control one or more of $r_1$, $r_2$, $r_3$ and the movement of the droplet receiver.

14. The device according to claim 13, wherein the automated system comprises at least one or more sensors, and/or one or more actuators.

15. The device according to claim 13, further comprising a comparison module configured to correlate sensor data to a set point value, and deliver an adjustment signal to an actuator to adjust the magnitude of the parameter controlled by the actuator, wherein the actuator controls evaporation rate $r_2$ and the droplet receiver movement.

16. The device according to claim 15, wherein the automated control system comprises a machine vision unit that sequentially acquires one or more images of the droplet, processes the acquired images to determine one or more droplet parameters; and communicates the parameters to the comparison module.

17. The device according to claim 11, further comprising a dilution module configured to dilute the received concentrated sample droplet in a second solvent or solvent blend to obtain a re-diluted sample.

18. A method of receiving a droplet, comprising:
(i) providing a droplet receiver comprising:
a receptacle for receiving a droplet;
a fluid conduit connected at a first end thereof to the droplet receptacle, thereby providing a course within which the droplet received in the droplet receptacle can move, the fluid conduit being at its distal end in fluid communication with a reservoir;
a fluid layer wetting the internal walls of the receptacle and conduit in such a way as to permit reception of the droplet without loss of the received droplet due to wetting of the internal receptacle and conduit walls; and
a pressure reduction unit configured to apply a reduced pressure to draw the received droplet into the reservoir; and
(ii) contacting and transferring the droplet into the receptacle.

19. The method according to claim 18, wherein contacting the droplet comprises moving the receptacle in a predetermined direction and at a predetermined speed.

20. The method according to claim 18, further comprising:
applying a reduced pressure to the received droplet to transport the droplet into the reservoir in fluid communication with the droplet receptacle.

* * * * *